(12) United States Patent
Reicher et al.

(10) Patent No.: US 8,626,527 B1
(45) Date of Patent: Jan. 7, 2014

(54) SYSTEMS AND METHODS FOR RETRIEVAL OF MEDICAL DATA

(75) Inventors: Murray A. Reicher, Rancho Santa Fe, CA (US); Evan K. Fram, Paradise Valley, AZ (US); Steven M. Greim, Oceanside, CA (US); Howard T. Lam, San Diego, CA (US)

(73) Assignee: DR Systems, Inc., San Diego, CA (US)

( * ) Notice: Subject to any disclaimer, the term of this patent is extended or adjusted under 35 U.S.C. 154(b) by 63 days.

(21) Appl. No.: 13/171,081

(22) Filed: Jun. 28, 2011

Related U.S. Application Data

(63) Continuation of application No. 11/265,979, filed on Nov. 3, 2005, now Pat. No. 7,970,625.

(60) Provisional application No. 60/625,690, filed on Nov. 4, 2004.

(51) Int. Cl.
  *G06Q 50/00* (2012.01)
(52) U.S. Cl.
  USPC .............................................................. 705/2
(58) Field of Classification Search
  USPC .................... 705/2, 3; 707/10, 100; 709/227; 725/105, 115
  See application file for complete search history.

(56) References Cited

U.S. PATENT DOCUMENTS

| | | |
|---|---|---|
| 4,672,683 A | 6/1987 | Matsueda |
| 5,123,056 A | 6/1992 | Wilson |
| 5,179,651 A | 1/1993 | Taaffe et al. |
| 5,431,161 A | 7/1995 | Ryals et al. |
| 5,452,416 A | 9/1995 | Hilton et al. |
| 5,542,003 A | 7/1996 | Wofford |
| 5,734,915 A | 3/1998 | Roewer |
| 5,740,267 A | 4/1998 | Echerer et al. |
| 5,779,634 A | 7/1998 | Ema et al. |
| 5,852,646 A | 12/1998 | Klotz et al. |
| 5,926,568 A | 7/1999 | Chaney et al. |
| 5,954,650 A | 9/1999 | Saito et al. |
| 5,976,088 A | 11/1999 | Urbano et al. |
| 5,986,662 A | 11/1999 | Argiro et al. |
| 5,987,345 A | 11/1999 | Engelmann et al. |
| 5,995,644 A | 11/1999 | Lai et al. |
| 6,115,486 A | 9/2000 | Cantoni |
| 6,128,002 A | 10/2000 | Leiper |
| 6,151,581 A | 11/2000 | Kraftson et al. |
| 6,175,643 B1 | 1/2001 | Lai et al. |

(Continued)

FOREIGN PATENT DOCUMENTS

WO    WO 2007/131157    11/2007

OTHER PUBLICATIONS

Office Action dated Dec. 1, 2011, in U.S. Appl. No. 13/228,349.
US 7,801,341, Sep. 2010, Fram et al. (withdrawn).

(Continued)

*Primary Examiner* — John Pauls
(74) *Attorney, Agent, or Firm* — Knobbe Martens Olson & Bear LLP

(57) ABSTRACT

A system and method for transmitting medical data. In one embodiment, a computer system receives filter criteria from a user of a first computer. Furthermore, the computer system may receive schedule information defining a schedule for checking for medical data. Depending on the embodiment, either the computer system or a remote server periodically selects, based upon the received schedule, medical data satisfying the received user-specific rules. The selected medical data is then transmitted to the computer system.

24 Claims, 5 Drawing Sheets

(56) References Cited

U.S. PATENT DOCUMENTS

| | | |
|---|---|---|
| 6,177,937 B1 | 1/2001 | Stockham et al. |
| 6,185,320 B1 | 2/2001 | Bick et al. |
| 6,243,095 B1 | 6/2001 | Shile et al. |
| 6,269,379 B1 | 7/2001 | Hiyama et al. |
| 6,304,667 B1 | 10/2001 | Reitano |
| 6,347,329 B1 | 2/2002 | Evans |
| 6,351,547 B1 | 2/2002 | Johnson et al. |
| 6,388,687 B1 | 5/2002 | Brackett et al. |
| 6,424,996 B1 | 7/2002 | Killcommons et al. |
| 6,438,533 B1 | 8/2002 | Spackman et al. |
| 6,463,169 B1 | 10/2002 | Ino et al. |
| 6,532,299 B1 | 3/2003 | Sachdeva et al. |
| 6,532,311 B1 | 3/2003 | Pritt |
| 6,556,695 B1 | 4/2003 | Packer et al. |
| 6,563,950 B1 | 5/2003 | Wiskott et al. |
| 6,574,629 B1 * | 6/2003 | Cooke et al. ............ 1/1 |
| 6,577,753 B2 | 6/2003 | Ogawa |
| 6,603,494 B1 | 8/2003 | Banks et al. |
| 6,606,171 B1 | 8/2003 | Renk et al. |
| 6,618,060 B1 | 9/2003 | Brackett |
| 6,630,937 B2 | 10/2003 | Kallergi et al. |
| 6,678,764 B2 | 1/2004 | Parvulescu et al. |
| 6,697,067 B1 | 2/2004 | Callahan et al. |
| 6,697,506 B1 | 2/2004 | Oian et al. |
| 6,734,880 B2 | 5/2004 | Chang et al. |
| 6,760,755 B1 | 7/2004 | Brackett |
| 6,775,402 B2 | 8/2004 | Bacus et al. |
| 6,778,689 B1 | 8/2004 | Aksit et al. |
| 6,820,100 B2 | 11/2004 | Funahashi |
| 6,829,377 B2 | 12/2004 | Milioto |
| 6,864,794 B2 | 3/2005 | Betz |
| 6,886,133 B2 | 4/2005 | Bailey et al. |
| 6,891,920 B1 | 5/2005 | Minyard et al. |
| 6,894,707 B2 | 5/2005 | Nemoto |
| 6,909,436 B1 | 6/2005 | Pianykh et al. |
| 6,909,795 B2 | 6/2005 | Tecotzky et al. |
| 6,917,696 B2 | 7/2005 | Soenksen |
| 6,996,205 B2 | 2/2006 | Capolunghi et al. |
| 7,016,952 B2 | 3/2006 | Mullen et al. |
| 7,022,073 B2 | 4/2006 | Fan et al. |
| 7,027,633 B2 | 4/2006 | Foran et al. |
| 7,031,846 B2 | 4/2006 | Kaushikkar et al. |
| 7,043,474 B2 | 5/2006 | Mojsilovic |
| 7,050,620 B2 | 5/2006 | Heckman |
| 7,054,473 B1 | 5/2006 | Roehrig et al. |
| 7,058,901 B1 | 6/2006 | Hafey et al. |
| 7,092,572 B2 | 8/2006 | Huang et al. |
| 7,103,205 B2 | 9/2006 | Wang et al. |
| 7,106,479 B2 | 9/2006 | Roy et al. |
| 7,110,616 B2 | 9/2006 | Ditt et al. |
| 7,113,186 B2 | 9/2006 | Kim et al. |
| 7,139,416 B2 | 11/2006 | Vuylsteke |
| 7,149,334 B2 | 12/2006 | Dehmeshki |
| 7,155,043 B2 | 12/2006 | Daw |
| 7,162,623 B2 | 1/2007 | Yngvesson |
| 7,170,532 B2 | 1/2007 | Sako |
| 7,174,054 B2 | 2/2007 | Manber et al. |
| 7,209,149 B2 | 4/2007 | Jogo |
| 7,212,661 B2 | 5/2007 | Samara et al. |
| 7,218,763 B2 | 5/2007 | Belykh et al. |
| 7,224,852 B2 | 5/2007 | Lipton et al. |
| 7,260,249 B2 | 8/2007 | Smith |
| 7,263,710 B1 | 8/2007 | Hummell et al. |
| 7,272,610 B2 | 9/2007 | Torres |
| 7,346,199 B2 | 3/2008 | Pfaff |
| 7,366,992 B2 | 4/2008 | Thomas, III |
| 7,412,111 B2 | 8/2008 | Battle et al. |
| 7,450,747 B2 | 11/2008 | Jabri et al. |
| 7,526,114 B2 | 4/2009 | Seul et al. |
| 7,526,132 B2 | 4/2009 | Koenig |
| 7,545,965 B2 | 6/2009 | Suzuki et al. |
| 7,583,861 B2 | 9/2009 | Hanna et al. |
| 7,613,335 B2 | 11/2009 | McLennan et al. |
| 7,634,121 B2 | 12/2009 | Novatzky et al. |
| 7,636,413 B2 | 12/2009 | Toth |
| 7,660,488 B2 | 2/2010 | Reicher et al. |
| 7,668,352 B2 | 2/2010 | Tecotzky et al. |
| 7,683,909 B2 | 3/2010 | Takekoshi |
| 7,698,152 B2 | 4/2010 | Reid |
| 7,716,277 B2 | 5/2010 | Yamatake |
| 7,787,672 B2 | 8/2010 | Reicher et al. |
| 7,834,891 B2 | 11/2010 | Yarger et al. |
| 7,885,440 B2 | 2/2011 | Fram et al. |
| 7,920,152 B2 | 4/2011 | Fram et al. |
| 7,953,614 B1 | 5/2011 | Reicher |
| 7,970,625 B2 | 6/2011 | Reicher et al. |
| 8,019,138 B2 | 9/2011 | Reicher et al. |
| 8,046,044 B2 | 10/2011 | Stazzone et al. |
| 8,065,166 B2 | 11/2011 | Maresh et al. |
| 8,094,901 B1 | 1/2012 | Reicher et al. |
| 8,217,966 B2 | 7/2012 | Fram et al. |
| 8,244,014 B2 | 8/2012 | Reicher et al. |
| 8,292,811 B2 | 10/2012 | Relkuntwar et al. |
| 8,380,533 B2 | 2/2013 | Reicher et al. |
| 8,457,990 B1 | 6/2013 | Reicher et al. |
| 2001/0016822 A1 | 8/2001 | Bessette |
| 2001/0042124 A1 * | 11/2001 | Barron ............ 709/227 |
| 2002/0016718 A1 | 2/2002 | Rothschild et al. |
| 2002/0021828 A1 | 2/2002 | Papier et al. |
| 2002/0039084 A1 | 4/2002 | Yamaguchi |
| 2002/0044696 A1 | 4/2002 | Sirohey et al. |
| 2002/0073429 A1 * | 6/2002 | Beane et al. ........ 725/105 |
| 2002/0091659 A1 | 7/2002 | Beaulieu et al. |
| 2002/0103673 A1 | 8/2002 | Atwood |
| 2002/0103827 A1 | 8/2002 | Sesek |
| 2002/0110285 A1 | 8/2002 | Wang et al. |
| 2002/0180883 A1 | 12/2002 | Tomizawa et al. |
| 2003/0005464 A1 * | 1/2003 | Gropper et al. ........ 725/115 |
| 2003/0028402 A1 | 2/2003 | Ulrich et al. |
| 2003/0037054 A1 * | 2/2003 | Dutta et al. ........ 707/100 |
| 2003/0065613 A1 | 4/2003 | Smith |
| 2003/0071829 A1 | 4/2003 | Bodicker et al. |
| 2003/0101291 A1 | 5/2003 | Mussack et al. |
| 2003/0115083 A1 | 6/2003 | Masarie et al. |
| 2003/0140141 A1 | 7/2003 | Mullen et al. |
| 2003/0187689 A1 | 10/2003 | Barnes et al. |
| 2003/0190062 A1 | 10/2003 | Noro et al. |
| 2003/0204420 A1 | 10/2003 | Wilkes et al. |
| 2004/0024303 A1 | 2/2004 | Banks et al. |
| 2004/0086163 A1 | 5/2004 | Moriyama et al. |
| 2004/0088192 A1 | 5/2004 | Schmidt et al. |
| 2004/0105574 A1 | 6/2004 | Pfaff |
| 2004/0114714 A1 | 6/2004 | Minyard et al. |
| 2004/0143582 A1 | 7/2004 | Vu |
| 2004/0161164 A1 | 8/2004 | Dewaele |
| 2004/0165791 A1 | 8/2004 | Kaltanji |
| 2004/0202387 A1 | 10/2004 | Yngvesson |
| 2004/0243435 A1 | 12/2004 | Williams |
| 2004/0252871 A1 | 12/2004 | Tecotzky et al. |
| 2004/0254816 A1 | 12/2004 | Myers |
| 2005/0027570 A1 | 2/2005 | Maier et al. |
| 2005/0043970 A1 | 2/2005 | Hsieh |
| 2005/0063575 A1 | 3/2005 | Ma et al. |
| 2005/0065424 A1 | 3/2005 | Shah et al. |
| 2005/0074157 A1 | 4/2005 | Thomas, III |
| 2005/0075544 A1 | 4/2005 | Shapiro et al. |
| 2005/0108058 A1 * | 5/2005 | Weidner et al. ............ 705/3 |
| 2005/0114178 A1 | 5/2005 | Krishnamurthy et al. |
| 2005/0114179 A1 | 5/2005 | Brackett et al. |
| 2005/0114283 A1 | 5/2005 | Pearson et al. |
| 2005/0184988 A1 | 8/2005 | Yanof et al. |
| 2005/0197860 A1 | 9/2005 | Joffe et al. |
| 2005/0238218 A1 | 10/2005 | Nakamura |
| 2005/0244041 A1 | 11/2005 | Tecotzky et al. |
| 2005/0273009 A1 | 12/2005 | Deischinger et al. |
| 2006/0008181 A1 | 1/2006 | Takekoshi |
| 2006/0031097 A1 | 2/2006 | Lipscher et al. |
| 2006/0058603 A1 | 3/2006 | Dave et al. |
| 2006/0093198 A1 | 5/2006 | Fram et al. |
| 2006/0093199 A1 | 5/2006 | Fram et al. |
| 2006/0095423 A1 | 5/2006 | Reicher et al. |
| 2006/0095426 A1 | 5/2006 | Takachio et al. |
| 2006/0111941 A1 | 5/2006 | Blom |
| 2006/0181548 A1 | 8/2006 | Hafey |

(56) References Cited

U.S. PATENT DOCUMENTS

| | | |
|---|---|---|
| 2006/0230072 A1 | 10/2006 | Partovi et al. |
| 2006/0241979 A1 | 10/2006 | Sato et al. |
| 2006/0277075 A1 | 12/2006 | Salwan |
| 2006/0282408 A1 | 12/2006 | Wisely et al. |
| 2007/0050701 A1 | 3/2007 | El Emam et al. |
| 2007/0055550 A1 | 3/2007 | Courtney et al. |
| 2007/0067124 A1 | 3/2007 | Kimpe et al. |
| 2007/0073556 A1 | 3/2007 | Lau et al. |
| 2007/0124541 A1 | 5/2007 | Lang et al. |
| 2007/0162308 A1 | 7/2007 | Peters |
| 2007/0174079 A1 | 7/2007 | Kraus |
| 2007/0192140 A1 | 8/2007 | Gropper |
| 2007/0239481 A1 | 10/2007 | DiSilvestro et al. |
| 2008/0059245 A1 | 3/2008 | Sakaida et al. |
| 2008/0103828 A1 | 5/2008 | Squilla et al. |
| 2008/0275913 A1 | 11/2008 | van Arragon et al. |
| 2009/0129643 A1 | 5/2009 | Natanzon et al. |
| 2009/0198514 A1 | 8/2009 | Rhodes |
| 2010/0138239 A1 | 6/2010 | Reicher et al. |
| 2010/0198608 A1 | 8/2010 | Kaboff et al. |
| 2010/0201714 A1 | 8/2010 | Reicher |
| 2010/0299157 A1 | 11/2010 | Fram et al. |
| 2011/0016430 A1 | 1/2011 | Fram |
| 2011/0267339 A1 | 11/2011 | Fram |
| 2011/0316873 A1 | 12/2011 | Reicher |
| 2012/0163684 A1 | 6/2012 | Natanzon et al. |
| 2012/0194540 A1 | 8/2012 | Reicher |
| 2013/0083023 A1 | 4/2013 | Fram |
| 2013/0159019 A1 | 6/2013 | Reicher |
| 2013/0169661 A1 | 7/2013 | Reicher |

OTHER PUBLICATIONS

Crowley, Rebecca et al., *Development of Visual Diagnostic Expertise in Pathology: an Information-processing Study*, Jan. 2003, Journal of the American medical Informatics Association, vol. 10, No. 1, pp. 39-51.
Non-Final Office Action dated Aug. 28, 2007 in U.S. Appl. No. 11/179,384.
Final Office Action dated Jun. 26, 2008 in U.S. Appl. No. 11/179,384.
Non-Final Office Action dated Dec. 29, 2008 in U.S. Appl. No. 11/179,384.
Final Office Action dated Jul. 24, 2009, in U.S. Appl. No. 11/179,384.
Notice of Allowance dated Nov. 3, 2009, in U.S. Appl. No. 11/179,384.
Non-Final Office Action dated Aug. 18, 2010 in U.S. Appl. No. 12/702,976.
Interview Summary dated Dec. 1, 2010, in U.S. Appl. No. 12/702,976.
Final Office Action dated Feb. 17, 2011 in U.S. Appl. No. 12/702,976.
Interview Summary dated May 31, 2011 in U.S. Appl. No. 12/702,976.
Notice of Allowance dated Jul. 20, 2011, in U.S. Appl. No. 12/702,976.
Non-Final Office Action dated Oct. 1, 2009, in U.S. Appl. No. 11/268,261.
Notice of Allowance dated Feb. 2, 2010, in U.S. Appl. No. 11/268,261.
Notice of Allowance dated May 17, 2010, in U.S. Appl. No. 11/268,261.
Supplemental Notice of Allowance dated Aug. 6, 2010, in U.S. Appl. No. 11/268,261.
Interview Summary dated May 14, 2010, in U.S. Appl. No. 11/268,261.
Issue Notice dated Sep. 2, 2010, in U.S. Appl. No. 11/268,261.
Notice of Allowance dated Oct. 8, 2010, in U.S. Appl. No. 11/268,261.
Notice of Allowance dated Dec. 3, 2010, in U.S. Appl. No. 11/268,261.
Office Action dated May 16, 2011, in U.S. Appl. No. 12/857,915.
Interview Summary dated Sep. 6, 2011, in U.S. Appl. No. 12/857,915.
Non-Final Office Action dated May 13, 2009, in U.S. Appl. No. 11/265,979.
Final Office Action dated Dec. 22, 2009 in U.S. Appl. No. 11/265,979.
Non-Final Office Action dated Jul. 8, 2010 in U.S. Appl. No. 11/265,979.
Interview Summary dated Mar. 4, 2010 in U.S. Appl. No. 11/265,979.
Interview Summary dated Nov. 16, 2010 in U.S. Appl. No. 11/265,979.
Final Office Action dated Dec. 23, 2010 in U.S. Appl. No. 11/265,979.
Interview Summary dated Mar. 17, 2011 in U.S. Appl. No. 11/265,979.
Notice of Allowance dated May 26, 2011 in U.S. Appl. No. 11/265,979.
Non-Final Office Action dated Aug. 24, 2009 in U.S. Appl. No. 11/268,262.
Non-Final Office Action dated Apr. 16, 2010 in U.S. Appl. No. 11/268,262.
Interview Summary dated Nov. 24, 2009 in U.S. Appl. No. 11/268,262.
Interview Summary dated May 12, 2010 in U.S. Appl. No. 11/268,262.
Final Office Action dated Oct. 28, 2010 in U.S. Appl. No. 11/268,262.
Interview Summary dated Dec. 1, 2010 in U.S. Appl. No. 11/268,262.
Notice of Allowance dated Dec. 1, 2010 in U.S. Appl. No. 11/268,262.
Notice of Allowance dated Feb. 25, 2011 in U.S. Appl. No. 11/268,262.
Non-Final Office Action dated Jul. 27, 2009 in U.S. Appl. No. 11/265,978.
Notice of Allowance dated Nov. 19, 2009 in U.S. Appl. No. 11/265,978.
Notice of Allowance dated Apr. 19, 2010 in U.S. Appl. No. 11/265,978.
Supplemental Notice of Allowance dated May 3, 2010 in U.S. Appl. No. 11/265,978.
Supplemental Notice of Allowance dated Aug. 3, 2010 in U.S. Appl. No. 11/265,978.
Non-Final Office Action dated May 5, 2011 in U.S. Appl. No. 12/870,645.
Non-Final Office Action dated May 26, 2010 in U.S. Appl. No. 11/942,674.
Interview Summary dated Jul. 26, 2010 in U.S. Appl. No. 11/942,674.
Final Office Action dated Nov. 26, 2010 in U.S. Appl. No. 11/942,674.
Interview Summary dated Mar. 2, 2011 in U.S. Appl. No. 11/942,674.
Notice of Allowance, dated Apr. 1, 2011 in U.S. Appl. No. 11/942,674.
Non Final Office Action dated Sep. 16, 2010 in U.S. Appl. No. 11/942,687.
Interview Summary dated Dec. 3, 2010 in U.S. Appl. No. 11/942,687.
Final Office Action, dated Apr. 5, 2011 in U.S. Appl. No. 11/942,687.
Non-Final Office Action dated Apr. 14, 2010 in U.S. Appl. No. 11/944,027.
Interview Summary dated May 13, 2010 in U.S. Appl. No. 11/944,027.
Final Office Action dated Dec. 23, 2010 in U.S. Appl. No. 11/944,027.
Interview Summary dated Mar. 31, 2011 in U.S. Appl. No. 11/944,027.
Non-Final Office Action dated Sep. 29, 2010 in U.S. Appl. No. 11/944,000.
Final Office Action dated Apr. 20, 2011 in U.S. Appl. No. 11/944,000.
Interview Summary dated Jun. 7, 2011 in U.S. Appl. No. 11/944,000.
Notice of Allowance dated Jan. 6, 2011, in U.S. Appl. No. 11/268,261.
Interview Summary dated Nov. 6, 2012 in U.S. Appl. No. 13/171,081.
Final Office Action dated Oct. 22, 2012 in U.S. Appl. No. 11/944,027.

(56) References Cited

OTHER PUBLICATIONS

Notice of Allowance dated Oct. 15, 2012 in U.S. Appl. No. 12/622,404.
US 8,208,705, Jun. 2012, Reicher et al. (withdrawn).
Notice of Allowance dated Feb. 6, 2012, in U.S. Appl. No. 13/228,349.
Notice of Allowance dated Jul. 20, 2012, in U.S. Appl. No. 13/228,349.
Final Office Action dated Dec. 15, 2011, in U.S. Appl. No. 12/857,915.
Office Action dated Jun. 12, 2012, in U.S. Appl. No. 12/857,915.
Non-Final Office Action dated Jan. 11, 2012 in U.S. Appl. No. 13/079,597.
Notice of Allowance dated Apr. 25, 2012, in U.S. Appl. No. 13/079,597.
Interview Summary, dated Feb. 17, 2012, in U.S. Appl. No. 13/118,085.
Final Office Action, dated Apr. 13, 2012, in U.S. Appl. No. 13/118,085.
Office Action dated Apr. 19, 2012 in U.S. Appl. No. 11/944,027.
Interview Summary dated Jun. 28, 2012 in U.S. Appl. No. 11/944,027.
Office Action dated Feb. 3, 2012 in U.S. Appl. No. 12/622,404.
Interview Summary dated May 8, 2012 in U.S. Appl. No. 12/622,404.
Final Office Action dated Aug. 6, 2012 in U.S. Appl. No. 12/622,404.
Mendelson, et al., "Informatics in Radiology—Image Exchange: IHE and the Evolution of Image Sharing," RadioGraphics, Nov.-Dec. 2008, vol. 28, No. 7.
Non-Final Office Action dated Apr. 4, 2013 in U.S. Appl. No. 13/535,758.
Non-Final Office Action dated May 31, 2013, in U.S. Appl. No. 13/345,606.
Interview Summary dated Aug. 15, 2013, in U.S. Appl. No. 13/345,606.
Notice of Allowance, dated Feb. 6, 2013, in U.S. Appl. No. 13/118,085.
Notice of Allowance dated Jun. 5, 2013 in U.S. Appl. No. 11/944,027.
Appeal Brief dated Mar. 4, 2013 in U.S. Appl. No. 11/944,000.
Examiners Answer dated Jun. 26, 2013 in U.S. Appl. No. 11/944,000.
Office Action dated Mar. 4, 2013 in U.S. Appl. No. 12/891,543.
Interview Summary dated Apr. 5, 2013 in U.S. Appl. No. 12/891,543.

* cited by examiner

FIG. 5

| Exams that meet Receivable Exam Criteria | | | | | | | | | | | |
|---|---|---|---|---|---|---|---|---|---|---|---|
| Patient ID | Site | Last Name | First Name | Sex | Age | Exam Date | Time | Mod | Exam Description | Status | Received | Completed |
| 2002003007 | DRS | LIVER | LAURA | F | 55 | 01/18/2005 | 12:13 | NM | CARD AD PR R S 1 SD | S | 100% | Yes |
| 2002003007 | DRS | LIVER | LAURA | F | 55 | 01/18/2005 | 12:31 | NM | CARD AD PR R S 1 SD | S | 100% | No |
| 2002003007 | DRS | LIVER | LAURA | F | 55 | 01/18/2005 | 12:36 | NM | CARD AD PR R S 1 SD | S | 100% | Yes |
| 58777 | DRS | WILLIAMS | CHARLES' | M | 16 | 01/21/2005 | 15:42 | MR | ABDOMEN | S | 100% | No |
| 685474 | DRS | WILLIAMS | CHARLES' | M | 11 | 01/21/2005 | 13:13 | NM | LUNG VQ SETTING | S | 52% | No |
| 685474 | DRS | WILLIAMS | CHARLES' | M | 11 | 01/21/2005 | 15:45 | CT | CTA - CIRCLE OF WILLIS | S | 50% | No |

Receive options....

500

Select All    Receive    Close

SYSTEMS AND METHODS FOR RETRIEVAL OF MEDICAL DATA

CROSS-REFERENCE TO RELATED APPLICATIONS

This application is a continuation of U.S. application Ser. No. 11/265,979, filed Nov. 3, 2005, entitled "SYSTEMS AND METHODS FOR RETRIEVAL OF MEDICAL DATA," which claims priority under 35 U.S.C. §119(e) to U.S. Provisional Application Ser. No. 60/625,690, filed on Nov. 4, 2004, each of which are hereby expressly incorporated by reference in their entirety.

BACKGROUND OF THE INVENTION

1. Field of the Invention

This invention relates to management and retrieval of medical images.

2. Description of the Related Art

Medical imaging is increasingly moving into the digital realm. This includes imaging techniques that were traditionally analog, such as mammography, x-ray imaging, angiography, endoscopy, and pathology, where information can now be acquired directly using digital sensors, or by digitizing information that was acquired in analog form. In addition, many imaging modalities are inherently digital, such as MRI, CT, nuclear medicine, and ultrasound. Increasingly these digital images are viewed, manipulated, and interpreted using computers and related computer equipment. Accordingly, there is a need for improved systems and methods of viewing and retrieving these digital images.

SUMMARY OF THE INVENTION

One embodiment comprises a method of retrieving medical data. The method comprises receiving user-specific rules from a user of a first computer. The user specific rules define criteria for exams to be retrieved by the first computer. The method also comprises receiving schedule information defining a schedule for checking for medical data and periodically selecting, based upon the received schedule, medical data satisfying the user-specific rules. In one embodiment, the selected medical data is retrieved from a second computer.

Another embodiment includes a system for retrieving medical data, the system comprises: a central processing unit; and an application module executing on the central processing unit, wherein the application module receives user-specific rules and an update schedule. The application module periodically selects medical data satisfying the received user-specific rules based upon the update schedule, and wherein the application module retrieves the selected medical data from a remote computer via a network.

BRIEF DESCRIPTION OF THE DRAWINGS

FIG. 5 is an exemplary graphical screen display that identifies for a user which documents have been transmitted to the computing system of FIG. 1.

DETAILED DESCRIPTION OF EMBODIMENTS OF THE INVENTION

Embodiments of the invention will now be described with reference to the accompanying figures, wherein like numerals refer to like elements throughout. The terminology used in the description presented herein is not intended to be interpreted in any limited or restrictive manner, simply because it is being utilized in conjunction with a detailed description of certain specific embodiments of the invention. Furthermore, embodiments of the invention may include several novel features, no single one of which is solely responsible for its desirable attributes or which is essential to practicing the inventions herein described.

One embodiment provides a computing system 100 for receiving and accessing medical related images and documents. In one embodiment the computing system 100 receives medical data from a remote computer, such as an imaging device 170, an image server 180, or other computing system at a medical facility 190. In one embodiment, if there is new information created by these devices, it is periodically downloaded to the computing system 100 based upon a user-specific rules and update schedule.

In one embodiment, the computing system 100 can be left unattended in "auto-receive" mode. This means that a user, such as a physician, typically will not have to wait for exams to download; the exams they are interested in will be available when the user accesses the computing system 100.

In one embodiment, as will be discussed further below, the user will be able to provide a set of rules ("auto-receive criteria") that determines which exams should be auto-received. For instance, the user may wish to only receive "MRI" exams. In one embodiment, authorization criteria set by an administrator can impose limits on the range or types of auto-receive criteria that can be specified. This may be beneficial to preserve patient confidentiality, as well as to control network congestion. For example, in one embodiment, a user can only specify exams for which he is one of the listed referring doctors. Another criteria can include that a user cannot auto-receive exams that are more than 2 weeks old.

In one embodiment, once information is auto-retrieved, an interface is provided that allows a user to mark the information as being "completed" or "reviewed." The "completed" or other such status marker may be visible in an exam grid that is displayed on a display connected to the computing system 100. This makes it easy for the user to track which retrieved information has been viewed. In one embodiment, the computing system 100 stores this information beyond the deletion of the exam so that an already-completed document will not be auto-received a second time.

Figure 1:
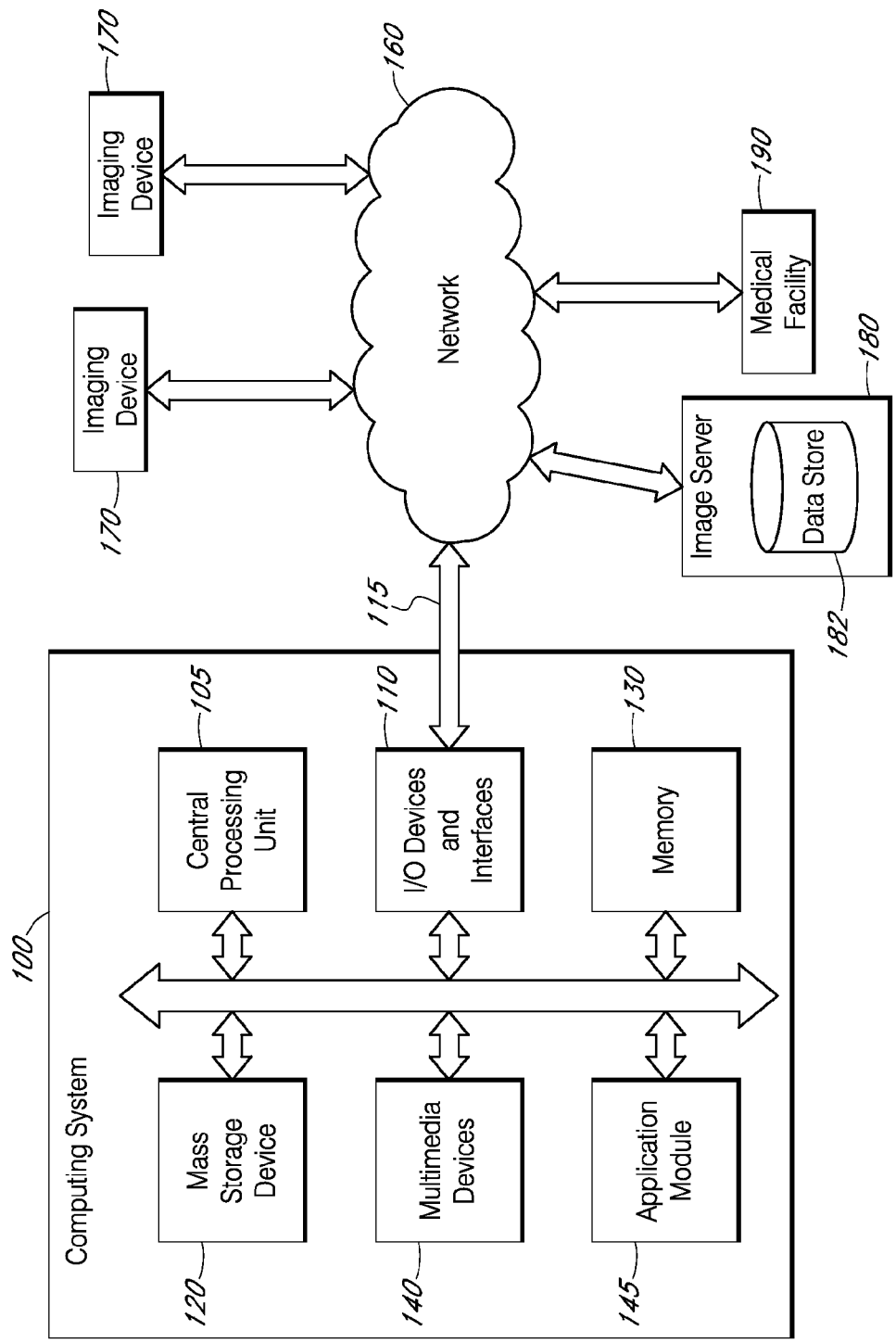
FIG. 1 is a block diagram of an exemplary computing system in communication with a network and various networked devices.

FIG. 1 is a block diagram of the computing system 100 in communication with a network 160 and various network devices. The computing system 100 may be used to implement certain systems and methods described herein. The functionality provided for in the components and modules of computing system 100 may be combined into fewer components and modules or further separated into additional components and modules.

In one embodiment, once information is auto-retrieved, an interface is provided that allows a user to mark the information as being "completed" or "reviewed." When reading is complete, an exam may be labeled "read," indicating that the medical professional has completed observation of the one or more medical images for purposes of creating a medical report. The "completed" or other such status marker may be visible in an exam grid that is displayed on a display connected to the computing system 100. This makes it easy for the user to track which retrieved information has been viewed. In one embodiment, the computing system 100 stores this information beyond the deletion of the exam so that an already-completed document will not be auto-received a second time.

The computing system 100 further includes a memory 130, such as random access memory ("RAM") for temporary storage of information and a read only memory ("ROM") for permanent storage of information, and a mass storage device 120, such as a hard drive, diskette, or optical media storage device. Typically, the modules of the computing system 100 are connected to the computer using a standards-based bus system. In different embodiments of the present invention, the standards based bus system could be Peripheral Component Interconnect (PCI), Microchannel, SCSI, Industrial Standard Architecture (ISA) and Extended ISA (EISA) architectures, for example.

The computing system 100 is generally controlled and coordinated by operating system software, such as the Windows 95, 98, NT, 2000, XP or other compatible operating systems. In Macintosh systems, the operating system may be any available operating system, such as MAC OS X. In other embodiments, the computing system 100 may be controlled by a proprietary operating system. Conventional operating systems control and schedule computer processes for execution, perform memory management, provide file system, networking, and I/O services, and provide a user interface, such as a graphical user interface ("GUI"), among other things.

The exemplary computing system 100 includes one or more of commonly available input/output (I/O) devices and interfaces 110, such as a keyboard, mouse, touchpad, and printer. In one embodiment, the I/O devices and interfaces 110 include one or more display devices, such as a monitor, that allows the visual presentation of data to a user. More particularly, display devices provide for the presentation of GUIs, application software data, and multimedia presentations, for example. In one embodiment, a GUI includes one or more display panes in which medical images may be displayed. According to the systems and methods described below, medical images may be stored on the computing system 100 or another device that is local or remote, displayed on a display device, and manipulated by the application module 145. The computing system 100 may also include one or more multimedia devices 140, such as speakers, video cards, graphics accelerators, and microphones, for example.

In the embodiment of FIG. 1, the I/O devices and interfaces 110 provide a communication interface to various external devices. In the embodiment of FIG. 1, the computing system 100 is coupled to a network 160, such as a LAN, WAN, or the Internet, for example, via a communication link 115. The network 160 may be coupled to various computing devices and/or other electronic devices. In the exemplary embodiment of FIG. 1, the network 160 is coupled to imaging devices 170, an image server 180, and a medical facility 190. In addition to the devices that are illustrated in FIG. 1, the network 160 may communicate with other computing, imaging, and storage devices.

The imaging devices 170 may be any type of device that is capable of acquiring medical images, such as an MRI, x-ray, mammography, or CT scan systems. The image server 180 includes a data store 182 that is configured to store images and data associated with images. In one embodiment, the imaging devices 170 communicate with the image server 182 via the network 160 and image information is transmitted to the image server 180 and stored in the data store 182. In one embodiment, the image data is stored in Digital Imaging and Communications in Medicine ("DICOM") format. The complete DICOM specifications may be found on the National Electrical Manufactures Association Website. Also, *NEMA PS 3—Digital Imaging and Communications in Medicine*, 2004 ed., Global Engineering Documents, Englewood Colo., 2004, provides an overview of the DICOM standard. Each of the above-cited references is hereby incorporated by reference in their entireties. In one embodiment, the data store 182 also stores the user-specific rules and an update schedule for determining when to search for new "medical data" to transmit to the computing system 100. As discussed in further detail below, the user-specific rules may vary depending upon user, type of application, or other factors.

"Medical data" is defined to include any data related to medical information, images, and patient information. As non-limiting examples, it may include but is not limited to a radiograph, computed tomography (CT), magnetic resonance imaging (MRI), Ultrasound (US), mammogram, positron emission tomography scan (PET), nuclear scan (NM), pathology, endoscopy, text files containing reports, voice files with results summaries, full digital dictation voice files for transcription, ophthalmology, or many other types of medical images. While this description is directed to retrieving and viewing of medical images, the methods and systems described herein may also be used in conjunction with non-medical images, such as, images of circuit boards, airplane wings, and satellite images, for example.

The exemplary image server 180 is configured to store images from multiple sources and in multiple formats. For example, the image server 180 may be configured to receive medical images in the DICOM format from multiple sources, store these images in the data store 182, and selectively transmit medical images to requesting computing devices.

The medical facility 190 may be a hospital, clinic, doctor's office, or any other medical facility. The medical facility 190 may include one or more imaging devices and may share medical images with the image server 180 or other authorized computing devices. In one embodiment, multiple computing systems, such as the computing system 100 may be housed at a medical facility, such as medical facility 190.

Figure 2:
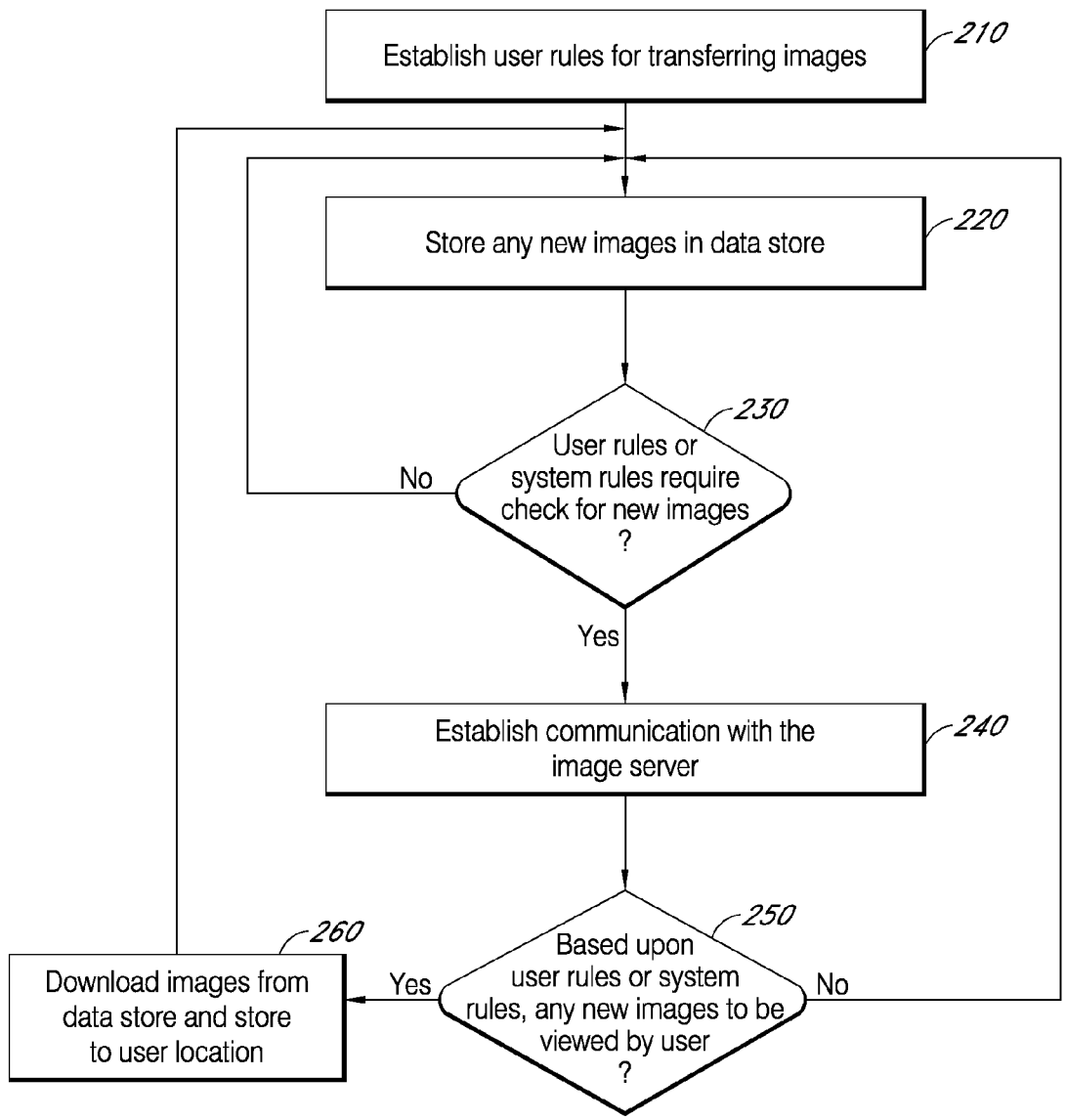
FIG. 2 is a flowchart illustrating a method of retrieving documents from a remote location based upon user-provided criteria.

FIG. 2 is a flowchart illustrating a method for transferring image data, wherein images are automatically retrieved based on user preferences. FIG. 2 illustrates an exemplary method for automatic transfer of medical images from the image server 180 to the medical facility 190 or to the computing system 100. As those of skill in art may appreciate, medical images are often high resolution, and thus, may require significant time to transfer from an imaging device or image storage device to the user's computing system. As described in further detail below, a user may establish a user specific set of rules that will determine how often the image server 180 is queried and which types of exams will be transmitted. Criteria may include, for example, the exam type, modality, time of day, and exam status. It is noted that the method of FIG. 2 can be controlled by doctors, their staff, transcriptionists, billers, and others.

With respect to FIG. 1, for example, images from multiple imaging devices 170 and facilities 190 may be stored on the data store 182 at image server 180. These images stored at the image server 180 may be marked for viewing by a remote user, such as by a doctor operating the computing system 100. Accordingly, the computing system 100 should, at some point prior to displaying the images stored on the image server 180, download the images to the mass storage device 120 of the computing system 100, for example. If a large number of images are marked for viewing by the user of the computing system 100, transfer of this large number of images may require a substantial amount of time. Accordingly, FIG. 2 provides an exemplary method for automatically transferring images to a desired computing system for later viewing.

It is noted that although FIG. 2 is directed to a process of downloading medical data directly to the computing system 100. In another embodiment, the medical data may be transmitted from a network 160 to a data store on a smaller network, e.g., which is quickly accessible by any of the computers on the network.

In a block 210, rules are established for transfer of images to various computing systems. In one embodiment, these rules comprise general system rules, and specific user rules for each reader, viewer, or user type. The rules may include criteria, or combinations of criteria, such as, time of day, date, physician name, exam type, modality, and various exams statuses, for example. As will be described in further detail below, these rules establish criteria for downloading images to specific computing systems. In one embodiment, general system rules are established and are used in the absence of specific user rules.

Figure 4:
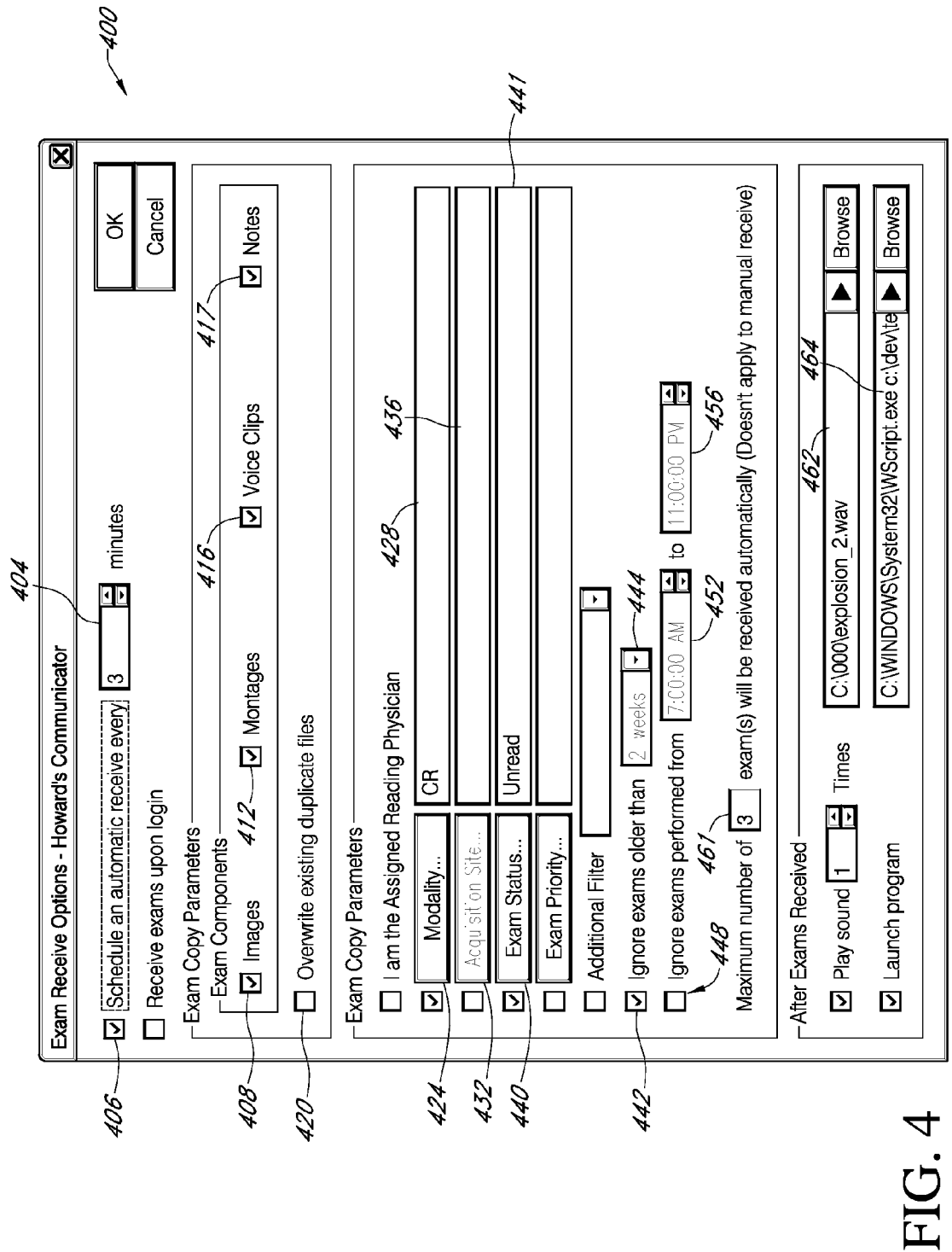
FIG. 4 is an exemplary graphical user interface that allows a user to define certain auto-receive criteria.

The rules established in block 210 may indicate that the image server 180 should be checked for new images every hour, for example. The rules may further indicate that, upon identifying images on the image server for listed patients, the images should be immediately downloaded to the reader's or viewer's computing system and stored on a mass storage device for later review by the physician, for example. In another embodiment, the rules may indicate that images with certain keywords in their file names should be downloaded, while any remaining images should not be downloaded. In another embodiment, the rules indicate that images are downloaded based on the imaging modality, and/or time of day acquired, and/or referring physician, and/or physician who performed the procedure, and/or user type, or other criteria. Accordingly, the rules may include both criteria for checking for new images and criteria for downloading new images. FIG. 4 illustrates a graphical specifying certain exemplary rules that may be defined by a user.

Continuing to a block 220, new images are stored in the data store 182 of the image server 180. As described above, these images may be received from countless image sources, including the imaging devices 170, the medical facility 190, and other medical imaging sources. In one embodiment, the image server 180 includes software and/or hardware that renames medical data.

Moving to a decision block 230, the computing device 100 determines if the rules require a check for new images on the image server 180. For example, a particular user rule may establish that a communication link with the image server 180 is established every day at 3:00 PM. Accordingly, as illustrated in FIG. 5, the decision block 230 continues to loop with block 220 until 3:00 PM each day. If block 230 determines that a check for new images is necessary, such as at 3:00 PM each day, for example, the method proceeds to a block 240.

At a block 240, a communication link is established with the image server 180 and the computing system 100 (or another computer that is locally networked to the computing system 100). In one embodiment, the image server 180 comprises multiple servers and other computing devices at multiple locations, where each of the servers and computing devices is in data communication with the network 160. Thus, at block 240, the communication link may be established between the computing system 100 and any other computing device that stores medical images. In one embodiment, the computing system 100 may periodically poll the imaging server 180 to determine if there is new medical data. In another embodiment, the communication link is initiated by the image server 180. In this embodiment, the communication link may be initiated only if there is new medical data satisfying the user-provided rules.

Moving to a decision block 250, the computing system 100 and/or the image server 180 determine if images are present on the image server 180 that should be downloaded to the computing system 100, based on the user rules and/or system rules. For example, if a user rule includes criteria selecting all images of specific patients that are stored on the image server 180, these images should be downloaded to the computing system 100. In another embodiment, if no user rules are established for a particular computing system 100, or a particular user of the computing system 100, the system rules may be applied in determining whether any images stored on the image server 180 should be downloaded to the computing system 100. For example, a system rule may include criteria indicating that only those images that are specifically marked for viewing by a particular user should be downloaded to that user's computing system 100.

It is desirable to allow a user or automated process with access to the image server 180 to explicitly mark cases for downloading by a particular machine, for example one serving a particular group of doctors, or by a particular physician. This could be accomplished by including fields in a database of exams on the image server 180 with this information. When a remote computer connects to the image server 180 to poll for exams to download, it would then download exams that had been marked for download by either that specific machine or exams that were marked for download by the physician logged into that machine. Optionally, the image server 180 could track when the exam had been successfully downloaded and viewed so that the exam would not be downloaded again when the user logged into a different machine.

If in the decision block 250, the computing system 100 and/or image server 180 determine that there are no images stored on the image server 180 that are to be transferred to the computing system 100, the method continues to block 220, where new images are stored in the mass storage device 120.

In the decision block 250, if it is determined that there are images stored on the server 180 that are to be transferred to the computing system 100, the method continues to block 260, where the images are transferred from the data store 182 to the computing system 100. If, for example, multiple images are transferred from the image server 182 to the computing system 100, significant time may be required for this transfer. Accordingly, by establishing rules that download images prior to the user's anticipated viewing time, the user may not be required to wait for the images to transfer from the image server 182 the computing system 100.

Figure 3:
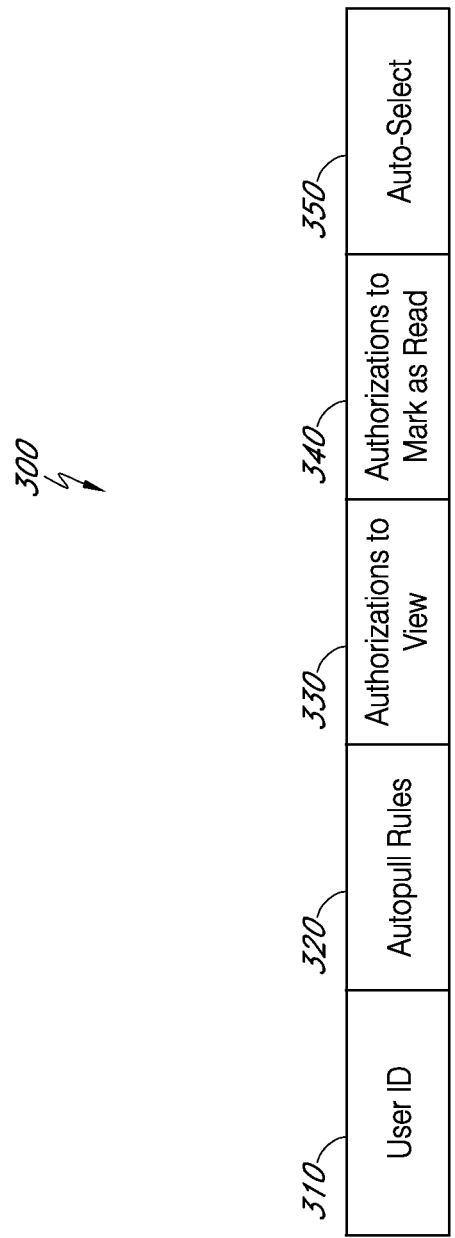
FIG. 3 is a block diagram illustrating an exemplary record that may be maintained with respect to the system of FIG. 1.

FIG. 3 illustrates an exemplary data rule data structure 300 that may be used to define the user-rules. The rule data structure 300 may be stored in a database. Depending on the embodiment, the rule data structure 300 may be located at the computing system 100 if the system is "pull driven," i.e., the computing system 100 polls a remote device to determine the availability of medical data. Alternatively, the rule data structure 300 may be located at the image server 180 if the system is "push driven," i.e., the image server 180 periodically determines whether to transmit data to the computing system 100. As is shown in FIG. 3, each user is assigned a user ID 310, which is recorded as a portion of the rule data structure 300. In one embodiment, the user ID 310 is an abbreviation of the user's name or a combination of the user's name and other text of characters. The exemplary data structure 300 includes auto-pull rules 320, which indicate the user's preferences for monitoring and downloading exams from remote computing devices, such as from the image server 380, for example. The auto-pull rules 320 may be in any known format, and may include various criteria for monitoring and transmitting image files. See the description of FIG. 2 for further discussion regarding generation and application of these rules. In addition to the above, the auto-pull rules 320 may established to retrieved medical data based upon any of the following criteria: modality (MRI, CT, X-ray etc); exam type (left knee X-ray, CT Chest, MRI Brain etc); notes type attached to exam (teaching note, ER note, quality assessment note, technologist note, scheduling note, etc); transcriptionist; exam priority (e.g., STAT, ASAP, LOW); ordered from (i.e., ordered from the emergency room, ICU); acquisition site (e.g. acquired at hospital #1 or imaging center #2); exam status (e.g., has the exam been read); archive status (has the exam been archived, archived and restored, not yet archived); assigned physician (has the exam been assigned to a particular physician for interpretation); reading physician (which doctor read the exam), ABN (ABN stands for advanced beneficiary notice—some exams may be marked because an ABN form is required from the patient), exam age (how long ago was the exam done); patient age; medical necessity (is the exam marked to indicate that a medical necessity is required); check-in-status (has the patient checked into the department—a record might exist even before images are acquired); confirmation required (a record can be created before an exam is performed—this criteria indicates that the exam has been marked to indicate that the patient should be called to confirm the exam); eligibility (this marker indicates whether insurance eligibility has been established); report status (has a text report been generated, transcribed, approved or other statuses); and report actions (has the completed report been faxed, stored, sent out to other systems).

Each of the foregoing filter criteria may be selected using simple or complex search expressions such "AND" or "OR." Complex filter criteria may be stored on the image server 180, then used by local devices that access these records via the web.

The authorizations to view rules 330 include criteria for determining which exams the user may view. For example, the authorizations to view rules 330 field for a hospital administrator may indicate that the administrator can view any exam stored on a computing device stored in the hospital or generated at the hospital.

The authorizations to mark as read rules 340 include criteria for determining if the user has rights to mark an exam as read. As discussed above, only authorized users should be allowed to mark an exam as read. In one embodiment, marking an exam as read indicates that the viewer has completed his review and evaluation of the exam. As those of skill in the art will recognize, if an exam is improperly notated as read, the physician, or other user, may not properly review the exam. Thus, ensuring that only authorized users are allowed to mark an exam as read reduces the likelihood that a physician fails to view an exam or inadvertently marks as read an examination he is authorized to view but not mark as read. Accordingly, using the exemplary data structure of FIG. 3, each user may be given specific rights to mark exams as read. For example, a MRI or x-ray technician may not have any rights to mark exams as read. However, a doctor may have rights to mark as read certain exam types.

The auto select rules 350 include criteria for automatically selecting related images for retrieval, based upon a current image that is viewed by the user. As non-limiting examples, a user may define a rule to retrieve any medical data that meets the following criteria: the medical data is created a certain day and/or time period, the medical data is stored in a particular location, and/or the medical data is related to a type of exam. Thus, in one embodiment, if the user is viewing selected medical data, other medical data is automatically retrieved from the image server 180 via the network 160 to the computing system 100. The retrieved medical data is selected based upon user-specific rules.

It is noted, that depending on the embodiment, portions of the data shown in FIG. 3 may be stored in separate data structures on the same or a different machine. For example, in one embodiment, auto-pull rules 320 are stored on the computer system 100 and the authorization information, e.g., authorizations to view 330 and authorizations to mark as read 340 are stored on the image server 180.

FIG. 4 is an exemplary graphical user interface 400 that may be used to receive auto-receive criteria from a physician. Depending on the embodiment, the layout of the graphical user interface, the types of input fields, buttons, and checkboxes may be modified.

Using the graphical user interface 400, a user may input a polling period in input window 404. The user may selectively enable and disable the auto-receive process via the use of checkbox 406. The user can select the types of files to be downloaded as well via checkbox 408 (images), checkbox 412 (montages), checkbox 416 (voice clips), and checkbox 417 (notes). The graphical user interface 400 could also be adapted to identify other types of information such as reports. The checkbox 420 allows a user overwrite duplicate files that may be retrieved if it is checked. A modality button 424 allows a user designate one or more modality criteria. In one embodiment, upon selection of the modality button 424, a pop-up screen illustrating all of the selectable modalities are displayed. Once selected, the designated modalities are displayed in a modality window 428. In one embodiment, the user may input a modality directly into the modality window 428.

In one embodiment, an acquisition site button 432 can be used to allow a user to identify the source of the auto-received information. In one embodiment, upon selection of the acquisition site button 432, a list of authorized locations are presented for user selection. After selection, the selected location is displayed in a location window 436. In one embodiment, an administrator can disable this function for selected users and may designate for a user or a group of users a predefined source location.

Furthermore, the user can identify which information should be retrieved based upon an "exam status" that is associated with the information to be retrieved, e.g., "read", "unread" or "either." In one embodiment, upon selection of an exam status button 440, a list of status types are presented for user selection. After selection, the selected types are displayed in a type window 441. In one embodiment, the user may input a selected status into the type window 441.

Using checkbox 442, a user can request to only receive information that has been generated within a predefined window of time up to the present day. The predefined window of time can be set by a user via the use of input window 444. Moreover, using checkbox 448, a user can select to auto-receive information that was created during a certain period of the day. The user can set the window of time via the use of input fields 452 (to provide a start time) and input field 456 (to provide an end time). Using an input field 461, the user can specify a maximum number of exams to be retrieved automatically.

Furthermore, using input fields 462 and 464, the user can designate the filename of an audio file to be played or a program to be executed. If an audio file is listed, the computing system 100 will play the audio file once information has been retrieved in accordance with the auto-receive criteria. If the user identified a program, it is executed after information has been auto-received. The program can make an audible alert or alternatively send an electronic message ("e-mail") to the user.

FIG. 5 is a screen display 500 illustrating an exemplary graphical user interface that may be used to show a user what documents have been received. In one embodiment, the screen display 500 illustrates which files have been "completed", i.e., reviewed by the user (see "completed" column). Furthermore, the screen display 500 shows what portion of the documents have been "received" via the network 160 (see "received" column). In one embodiment, the completed or receive status may alternatively be shown by check mark, highlight, or other image marking proximate to or on the respective record.

The foregoing description details certain embodiments of the invention. It will be appreciated, however, that no matter how detailed the foregoing appears in text, the invention can be practiced in many ways. For example, the above-described auto-retrieve may be performed on other types of images, in addition to medical images. For example, images of circuit boards, airplane wings, and satellite imagery may be analyzed using the described systems. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A method of retrieving medical data, the method comprising:
    receiving, via a user interface displayed on a user computing device, at least a first rule indicating types of medical data to be copied to the user computing device and a second rule indicating one or more of a modality, acquisition site, exam status, keywords in an exam description, or exam priority of medical data to be copied to the user computing device;
    determining, by the user computing device, rights of a user operating the user computing device to view medical data of respective patients, wherein users have varying rights to view respective medical data based on at least their respective medical training and/or their associations with respective medical data;
    selecting, by the user computing device, respective medical data for copying to the user computing device from a remote network accessible storage device in response to at least determining that the user has rights to view the respective medical data and the respective medical data matches the first rule and the second rule; and
    initiating transfer of the selected respective medical data for display on the user computing device.

2. The method of claim 1, wherein rights of the user to view medical data are determined based on an identity of the user.

3. The method of claim 1, wherein the associations with respective medical data indicates whether the user is a referring physician associated with the medical data.

4. A method comprising:
    receiving, via a user interface displayed on a user computing device, at least a first rule indicating types of medical data to be copied to the user computing device;
    determining, by the user computing device, rights of a user operating the user computing device to view medical data of respective patients, wherein users have varying rights to view respective medical data based on at least their respective medical training and/or their associations with respective medical data;
    determining rights of the user to mark the respective medical data as read, wherein marking respective medical data as read indicates that the user has completed observation of the respective medical data for purposes of creating a medical report, and wherein rights to mark respective medical data as read are based at least on the user's association with the respective medical data;
    selecting respective medical data for copying to the user computing device from a remote network accessible storage device in response to at least determining that the user has rights to view the respective medical data; and
    initiating transfer of the selected respective medical data for display on the user computing device.

5. A computing system comprising:
    a first computer comprising an interface that can access one or more storage devices via one or more networks;
    an application module configured for execution by the first computing system to:
        determine, based on an identity of a user of the first computer, rights that the specific user has to retrieve medical data of patients; and
        generate a user interface that enables selection of first criteria for retrieving medical data for use at the first computer, the first criteria including an indication of a frequency that the user would like the first computing system to poll the one or more storage devices to identify medical data matching other criteria including at least one of whether the medical data:
            has been reviewed by a user of the first computing system;
            has been observed for purposes of creating a medical report;
            has an associated indication of urgency;
            includes medical images;
            includes images from a particular imaging modality;
            includes a medical report;
            includes key selected images;
            includes audio;
            includes text notes;
            was acquired within a certain time period; or
            was obtained at a particular acquisition site;
        in accordance with the indicated frequency, periodically poll by the first computing system, without user intervention, the one or more storage devices for medical data matching the other criteria; and
        automatically retrieve, by the first computing system, any medical data matching the selected criteria from the one or more storage devices.

6. The computing system of claim 5, wherein respective of the medical data has attributes comprising more than one of the criteria in a Boolean AND or OR relationship.

7. The computing system of claim 5, wherein the automatically retrieving is further based on whether the user is authorized to retrieve the medical data that matches the selected criteria based on the rights associated with the specific user.

8. The computing system of claim 5, wherein the automatically retrieving allows the user to retrieve medical data at any location or using any computer.

9. The computing system of claim 5, wherein the application module is executed on the first computer.

10. The computing system of claim 5, wherein the application module is executed on a second computer associated with one or more of the storage devices.

11. The computing system of claim 5, wherein the rights to retrieve medical data are determined based on individual patients associated with respective medical data, a role of the user, an exam type of respective medical data, a modality of respective medical data, and/or a location of service associated with respective medical data.

12. The computing system of claim 5, wherein second criteria also associated with the first user and different than the first criteria, are associated with a second computer and are usable by the second computer to automatically retrieve medical data for transmission to the second computer based on a second indicated frequency and second other criteria associated with the second computer.

13. The computing system of claim 12, wherein the first criteria and the second criteria are each provided by the specific user.

14. The computing system of claim 12, wherein the second computer is operated by a second user.

15. The computing system of claim 14, wherein the first criteria and the second criteria are set by the specific user.

16. The computing system of claim 12, wherein the specific user is a radiologist or referring doctor.

17. The computing system of claim 5, wherein the user interface further enables selection of criteria for whether matching medical data should be retrieved upon login by the user.

18. A computing system comprising:
a first computer and a second computer each having one or more storage devices configured to store modules including software instructions and
one or more hardware computer processors configured to execute the modules, wherein the first computer includes
a first application module configured to:
access first rules stored on the first computer indicating rights and/or preferences of a user of the first computer to retrieve medical data to the first computer, wherein the first rules are configured specifically for use by the first computer;
access a first schedule stored on the first computer indicating one or more first times when medical data should be retrieved from one or more remote storage devices to the first computer;
at the one or more first times indicated by the first schedule, identifying respective medical data stored on the one or more remote storage devices matching the first rules, without user intervention; and
retrieving by the first computer, without user intervention, the identified respective medical data from the remote storage device and wherein the second computer includes a second application module configured to:
access second rules stored on the second computer indicating rights and/or preferences of the user to retrieve medical data to the second computer;
access a second schedule stored on the second computer indicating one or more second times when medical data should be retrieved from one or more remote storage devices to the second computer;
at the one or more second times indicated by the second schedule, identifying respective medical data stored on the one or more remote storage devices matching the second rules, without user intervention; and
retrieving by the second computer, without user intervention, the identified respective medical data from the remote storage device;
wherein the first and second rules and the first and second schedules are configured by the user specifically for use by the first and second computer, respectively; and
wherein the first rules on the first computer are different than the second rules on the second computer.

19. The computing system of claim 18, wherein the access rules further include storage locations specified by the user for storage of respective types of medical data.

20. The computing system of claim 18, wherein the access rules indicate that the user is authorized to retrieve medical data for which the user is the referring doctor.

21. The computing system of claim 18, wherein the application module is further configured to:
determine rights of the user to mark respective medical data as viewed; and
allow the user to mark respective medical data as viewed in accordance with the determined rights.

22. The computing system of claim 18, wherein the application module is further configured to:
determine rights of the user to mark respective medical data as read; and
allow the user to mark respective medical data as read in accordance with the determined rights.

23. The computing system of claim 18, wherein the application module is further configured to provide an audible and/or visual alert to the user in response to retrieving the identified respective medical data.

24. A non-transitory computer readable medium storing software instructions configured for execution on each of a first computer and a second computer operated by a user, the software instructions configured to cause the first computer to:
access first rules stored on the first computer indicating rights and/or preferences of the user to retrieve medical data to the first computer, wherein the first rules are configured specifically for use by the first computer;
access a first schedule stored on the first computer indicating one or more first times when medical data should be retrieved from one or more remote storage devices to the first computer;
at the one or more first times indicated by the first schedule, identifying respective medical data stored on the one or more remote storage devices matching the first rules, without user intervention; and
retrieving by the first computer, without user intervention, the identified respective medical data from the remote storage device; and
the software instructions are further configured to cause the second computer to:
access second rules stored on the second computer indicating rights and/or preferences of the user to retrieve medical data to the second computer;
access a second schedule stored on the second computer indicating one or more second times when medical data should be retrieved from one or more remote storage devices to the second computer;
at the one or more second times indicated by the second schedule, identifying respective medical data stored on the one or more remote storage devices matching the second rules, without user intervention; and
retrieving by the second computer, without user intervention, the identified respective medical data from the remote storage device;

wherein the first and second rules and the first and second schedules are configured by the user specifically for use by the first and second computer, respectively; and wherein the first rules on the first computer are different than the second rules on the second computer.

* * * * *